United States Patent
Durell, Jr.

(10) Patent No.: US 6,428,471 B1
(45) Date of Patent: Aug. 6, 2002

(54) VARIABLE VIEW ARTHROSCOPE

(76) Inventor: William E. Durell, Jr., 52 Candlewood Dr., North Barrington, IL (US) 60010

(*) Notice: Subject to any disclaimer, the term of this patent is extended or adjusted under 35 U.S.C. 154(b) by 147 days.

(21) Appl. No.: 09/644,360

(22) Filed: Aug. 23, 2000

Related U.S. Application Data (63) Continuation of application No. 09/243,845, filed on Feb. 3, 1999, now Pat. No. 6,110,105.

(51) Int. Cl.[7] .................................................. A61B 1/00
(52) U.S. Cl. ........................ 600/173; 600/130; 600/131
(58) Field of Search ................................. 600/173, 176, 600/130, 131, 106, 107; 385/119; 433/30

(56) References Cited

U.S. PATENT DOCUMENTS

| | | | | |
|---|---|---|---|---|
| 3,804,081 A | * | 4/1974 | Kinoshita et al. | 385/119 |
| 4,697,577 A | * | 10/1987 | Forkner | 600/173 |
| 4,750,475 A | * | 6/1988 | Yoshihashi | 600/131 |
| 5,738,631 A | * | 4/1998 | Konstorum | 600/146 |
| 6,007,484 A | * | 12/1999 | Thompson | 600/122 |
| 6,019,721 A | * | 2/2000 | Holmes et al. | 433/29 |

* cited by examiner

*Primary Examiner*—John P. Leubecker
(74) *Attorney, Agent, or Firm*—Cook, Alex, McFarron, Manzo, Cummings & Mehler, Ltd.

(57) ABSTRACT

A variable-view arthroscope or like instrument (endoscope, etc.) includes an elongated housing tube extending from an outer control end to an inner image input end that is closed by an input lens; the input lens preferably is a diverging lens. In the form shown in FIGS. 6A–6C, the input lens has a concave inner surface and a concave outer surface. A lighting apparatus illuminates a surgical working area beyond the image end of the housing tube; the illumination may be projected outwardly through the input lens. A movable mirror intercepts light reflected from the surgical working area to produce a working image that is reflected to a fixed mirror that in turn reflects the working image to impinge upon the input end of a relay lens assembly. The working image is transmitted to a receptor, which is located near the outer (control) end of the housing tube. The relay lens applies the image to an image device, such as a conventional CCD unit, that transmits the image to a location exterior to the scope. A control member, shown as a control rod extending longitudinally within the housing tube, varies the position of the movable mirror between first and second limits, adding about 30° or more to the image available to a user of the instrument.

13 Claims, 11 Drawing Sheets

VARIABLE VIEW ARTHROSCOPE

This application is a continuation of application Ser. No. 09/243,845 now U.S. Pat. No. 6,110,105, filed Feb. 3, 1999 which prior application is incorporated by reference.

BACKGROUND OF THE INVENTION

Arthroscopes and other like optical instruments, such as endoscopes, have long been known in the field of surgery and in other fields. In this specification and in the appended claims the term "arthroscope" means and should be interpreted to include an endoscope or any other like optical instrument, whether used for surgery or otherwise. In this application, the invention is described in connection with an instrument employed for surgery, as in human surgery.

Over the last fifteen or more years the nature of surgery has changed substantially, with minimally invasive surgery becoming a mainstay. Within the orthopedic community, in particular, arthroscopy and similar techniques have become the most common surgical procedures. Surgery using such techniques is less painful for the patient and, in most instances, can be performed more quickly and safely than with techniques that require greater invasion of the patient's body; anesthesia is also less complicated, the surgery can often be handled on an outpatient basis, and the procedures are better from the standpoint of cost effectiveness. Patients return to normal life more quickly, and hospital stays may be reduced in length or even eliminated. However, all of these benefits are available only if the minimally invasive surgery allows for better diagnostic capabilities, improved surgical techniques, and reduced iatrogenic damage. Similar benefits are available with other, non-surgical, instruments.

One problem in these minimally invasive techniques derives from limitations in the arthroscopes, endoscopes and other principal optical instruments employed. In particular, the rather limited field of view afforded by even the best instruments commercially available in 1998 has inhibited progress to at least some extent; available instruments and techniques have not changed dramatically since 1985. A substantial improvement in the field of view available to a person employing an arthroscope or like instrument for exploratory or repair procedures is much needed.

Several techniques for modification (widening) of the view offered by arthroscopic/endoscopic instruments have been proposed, but they have not been especially successful. Generally, such proposals have required packing a plurality of movable lenses or prisms into the input end of the instrument; the resulting problems of precision of construction, precision of relative movements, space requirements, optical distortions, and elimination of undesired "ambient" light have been substantial. This is not particularly surprising; interaction between the prisms and lenses involved, along with light loss, exacerbates the problem.

SUMMARY OF THE INVENTION

It is an object of this invention, therefore, to provide a new and improved arthroscope that affords the user a broadened effective field of view with few or no added lenses or prisms, a minimum of movable parts, and no requirement for movement of the instrument to vary its scope of view.

A related object of the invention is to afford a new and improved arthroscope that is relatively simple and effective in construction, cost efficient and durable, yet has an improved and expanded field of view.

Accordingly, the invention relates to a variable view arthroscope comprising an elongated housing having an image input end spaced from an outer control end. An input lens, preferably a diverging type lens, closes (and usually seals) the image input end of the housing tube, which is beveled at an angle of 30° to 60°. Lighting means are provided for illuminating a working image area beyond the image input end of the housing tube. An input lens, located in the input end of the housing tube, intercepts light reflected back from the working area. That reflected light constitutes a working image. The light image reflected from the working area back through the input lens is directed to a movable mirror. The movable mirror may be rotatable or it may move linearly. There is a control member, usually an elongated control rod, for varying the position of the movable mirror to any position or to a series of fixed positions between a first limit position and a second limit position. A fixed mirror is positioned to intercept light from the movable mirror, re-directing that light toward a relay lens located near the fixed mirror position. A relay lens assembly directs the light image from the fixed mirror through the length of the relay lens assembly to impinge upon a focusing lens assembly. The focusing lens assembly consists of focusing and zoom lens and their controls and is preferably located in the control portion of the arthroscope.

DESCRIPTION OF THE PREFERRED EMBODIMENTS

One preferred embodiment of the invention is illustrated as an arthroscope 30, shown in FIGS. 1–10.

Figure 1:
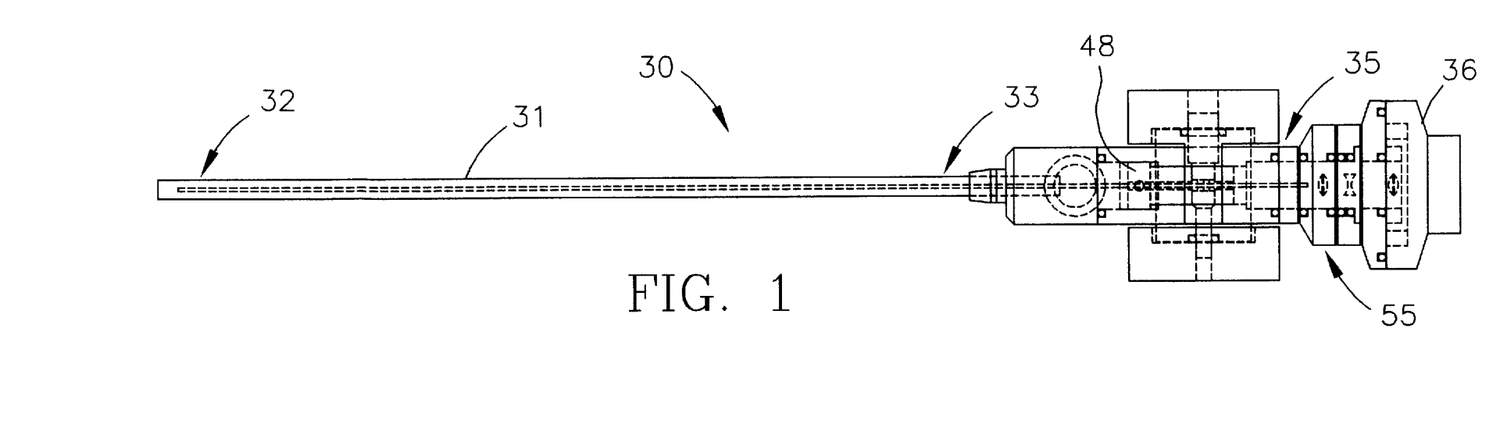
FIG. 1 is a plan view of a variable view arthroscope constructed in accordance with a preferred embodiment of the invention.
Figure 2:
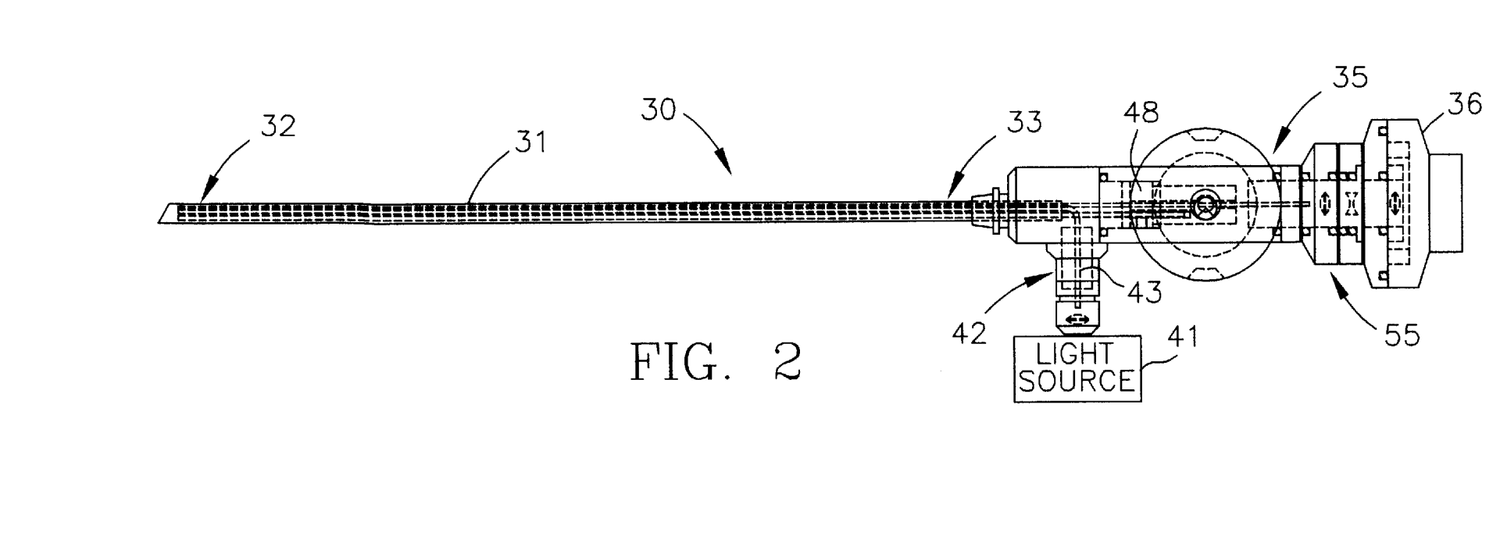
FIG. 2 is an elevation view of the instrument of FIG. 1.
Figure 3:
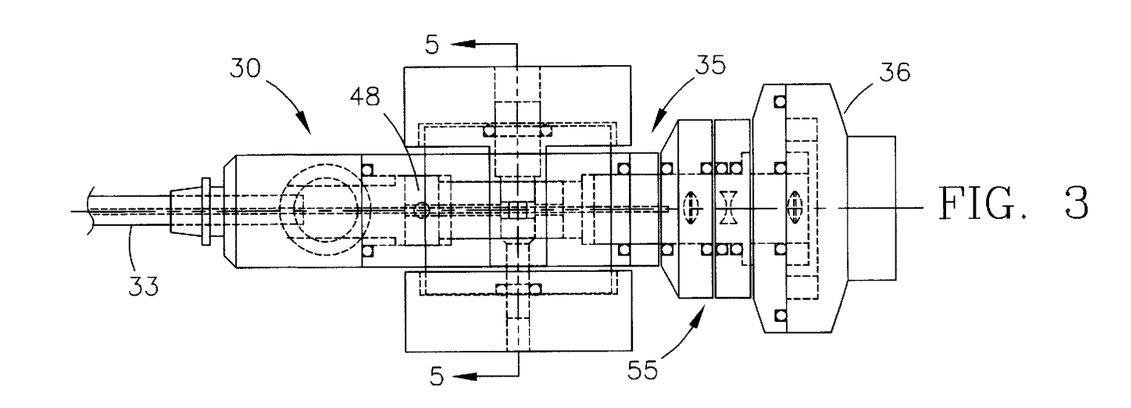
FIG. 3 is a plan view, on an enlarged scale, of the control portion of the arthroscope of FIGS. 1 and 2.

As shown in FIGS. 1 and 2, arthroscope 30 includes an elongated housing tube 31, which has an image input end 32 and a control end 33. Housing tube 31, and more specifically its control end 33, may extend into the outer control portion 35 of arthroscope 30, shown in greater detail in FIGS. 3–5. As shown in FIGS. 1–4, the control portion 35, from which the control end 33 of the housing tube 31 of arthroscope 30 projects, ends with a CCD attachment 36. The CCD attachment 36 is connected by appropriate means to an image screen (not shown) to be viewed by a person using arthroscope 30. Because CCD attachment 36 may be of conventional construction and does not constitute a part of the present invention, it has not been shown in detail.

Figure 6A:
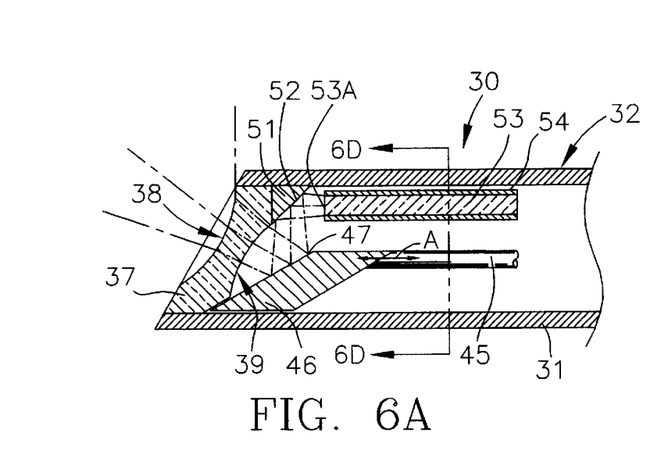
FIG. 6A is a sectional, longitudinal elevation view, on an enlarged scale, of the image input end of the arthroscope of FIG. 1, adjusted for a maximum upward view.
Figure 6B:
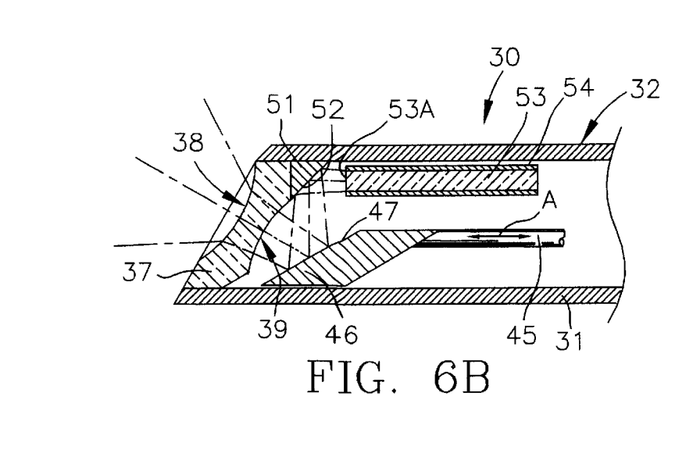
FIG. 6B is a sectional elevation view, like FIG. 6A, of the image input end of the arthroscope of FIG. 1, adjusted for an intermediate view.
Figure 6C:
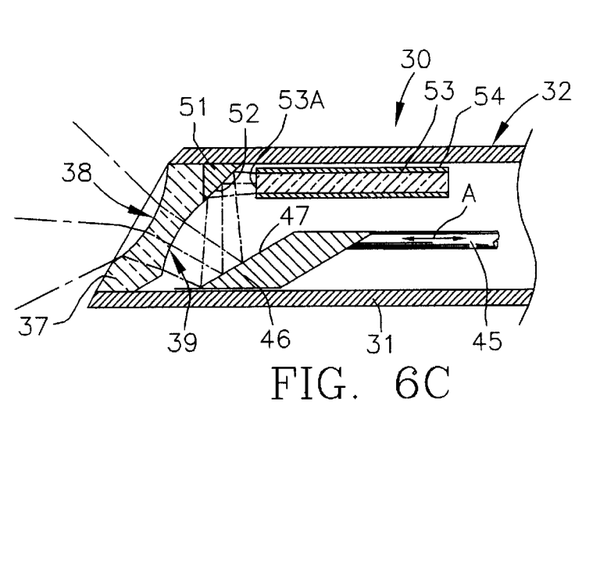
FIG. 6C is a sectional elevation view, like FIGS. 6A and 6B, of the image input end of the arthroscope of FIG. 1, adjusted for a maximum downward view.
Figure 6D:
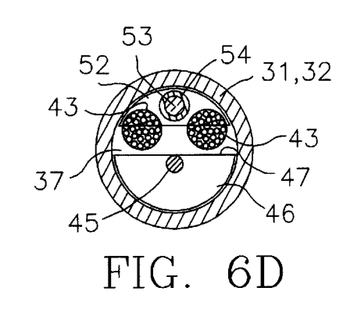
FIG. 6D is a sectional view taken approximately along line 6D—6D in FIG. 6A.

As best shown in FIG. 2 and in the enlarged views of FIGS. 6A–6C, the image input end 32 of housing tube 31 is of beveled construction at its extreme end; the bevel is usually between 30° and 60°. The outer end of housing tube 31, shown in enlargement in FIGS. 6A–6C, is closed by a diverging input lens 37 (plural lenses may be used). Input lens 37 is shown as having an outer concave surface 38 spaced from an inner concave surface 39. Input lens 37 is preferably sealed into the tip of the input end 32 of housing tube 31; a suitable seal material to mount lens 37 in place in the end of housing tube 31 is any conventional sealing adhesive approved by the FDA for in vivo use. Input lens (or lenses) 37 may be formed of optical glass or any other suitable lens material. When a single input lens is used, input lens 37 preferably has a rim matched as closely as possible to the inside diameter of the housing tube 31 at its image input end 32 to assure a good seal between the housing tube and the input lens. Similar expedients should be employed if plural input lenses are utilized.

Figure 4:
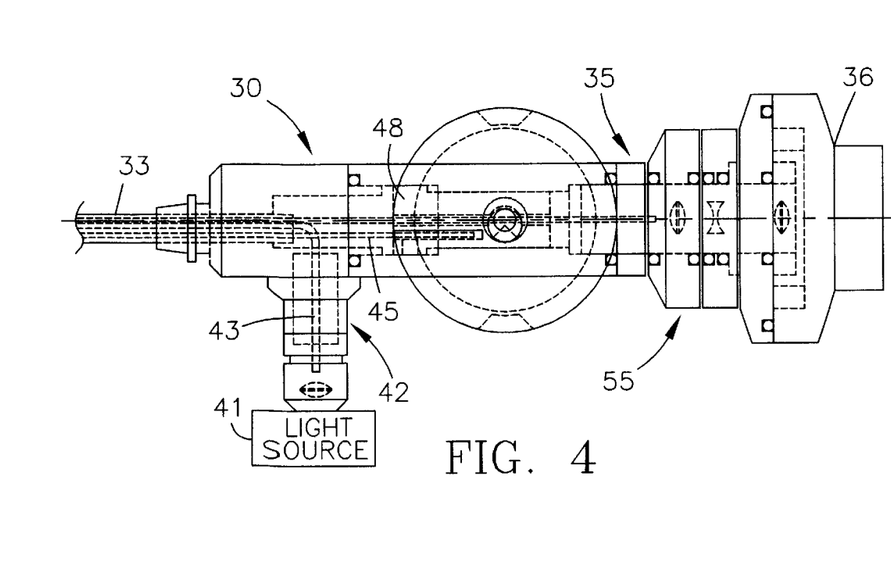
FIG. 4 is an elevation view, on an enlarged scale, of the control portion of the instrument of FIGS. 1 and 2.
Figure 5:
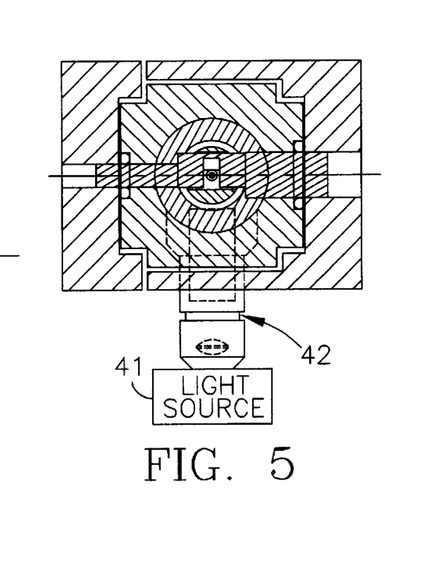
FIG. 5 is a detail view taken approximately as indicated by line 5—5 in FIG. 3.

Arthroscope 30 includes, an outer control portion 35 and a light source 41 that is connected to a lighting means or apparatus 42; see FIGS. 2 and 4. The lighting assembly 42 includes one or more optic fiber bundles 43; the fiber optic bundle (or bundles) extend to the input end of the arthroscope; see FIGS. 4 and 6D. The optic fiber bundles 43 have been omitted in FIGS. 6A–6C (and in other Figures) because they may be conventional in construction. The lighting assembly 42 is utilized to illuminate a surgical working area (not indicated) beyond the image input end 32 of the housing tube; illumination of the surgical working area may be made through the input lens 37.

A control member, shown in FIG. 4 as a control rod 45, extends longitudinally through the housing tube 31 from outer control portion 35 to its input end 32. Rod 45 is used to vary the position of a slidably movable mirror (See arrows A in FIGS. 6A–6C) having a base 46 and a mirror surface 47 along the axis of rod 45. Mirror surface 47 is shown as planar in the drawings, but the movable mirror may be concave or other shapes. The mirror surface 47 is aligned with but spaced from the inner surface 39 of input lens 37. See FIGS. 6A–6C. The end of control rod 45 is affixed to the movable mirror base 46, as best shown in the enlarged views of FIGS. 6A–6C. A suitable commercially available adhesive may be used to join the end of rod 45 to the base 46 of the movable mirror; alternatively, soldering or brazing may be used if desired. The tip of control rod 45 may be polished and coated to afford a suitable movable mirror, eliminating the need for a separate part 46.

At the control end 35 of the arthroscope 30 the control rod 45 extends into and engages a slide 48. Slide 48 is driven linearly by means of two control knobs 49 and 50, as described hereinafter in connection with FIGS. 9A–9C.

In the arthroscope 30, as best shown in FIGS. 6A–6C, the base 46 of the movable mirror 46, 47 slides linearly between a maximum upward view position (FIG. 6A), through an intermediate position (FIG. 6B), to a maximum downward view position (FIG. 6C). Of course, the movement of the movable mirror base 46 may be reversed, moving from its maximum downward position (FIG. 6C) toward its maximum upward position (FIG. 6A). The images that may be provided to a surgeon by the arthroscope 30 all overlap. The maximum upward view of FIG. 6A, with movable mirror 46, 47 advanced by control rod 45 to a position immediately adjacent input lens 37, has an overlap of about fifty percent with the maximum downward view (FIG. 6C) afforded when the sliding mirror 46, 47 is fully retracted.

At the top of the input end of arthroscope 30, as seen in FIGS. 6A–6C, there is a fixed mirror comprising a. base 51 and a reflective (mirror) surface 52. The fixed mirror surface 52 intercepts a light image from the movable mirror surface 47 and re-directs that light image to impinge upon the input end 53A of a relay lens assembly 53. Relay lens assembly 53, FIGS. 6A–6C, may be of conventional construction having an outer stainless sleeve 54 for stability and directs the light toward a receptor, shown as a focusing lens assembly 55 (FIGS. 1, 2, 3 and 4). The focusing lens assembly 55 consists of focusing and zoom lens and is of conventional design. The focusing lens assembly 55 directs the light image in the customary manner, into the CCD attachment 36; see FIGS. 14. A slide 48 is located in the control portion 35 of arthroscope 30; the slide, shown in FIGS. 7A–7C, comprises a main body 57 having an axial relay lens opening 58, the relay lens opening 58 also extends through an enlarged end 59 of the slide. A socket 61 also in slide 48, formed to align and attach control rod 45 to slide 48, is best shown in FIG. 7B. The control rod socket 61, in the illustrated embodiment, is located directly below the axial opening 58 for the relay lens.

Figure 7A:
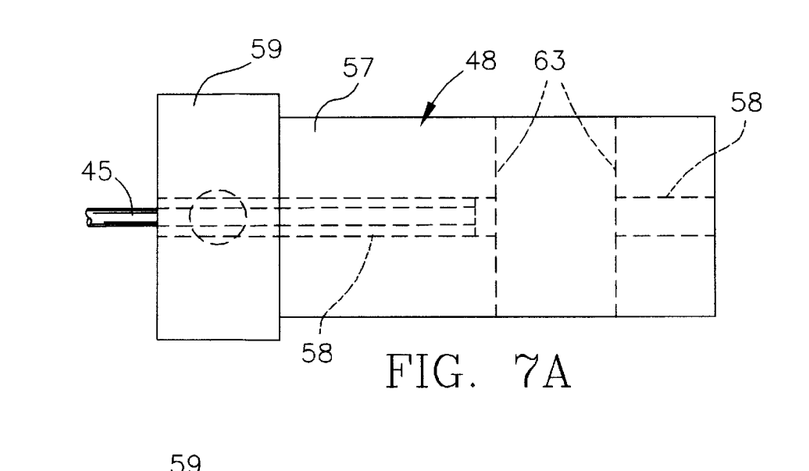
FIG. 7A is an elevation view, on an enlarged scale, of a slide member used in the arthroscope of FIG. 1.
Figure 7B:
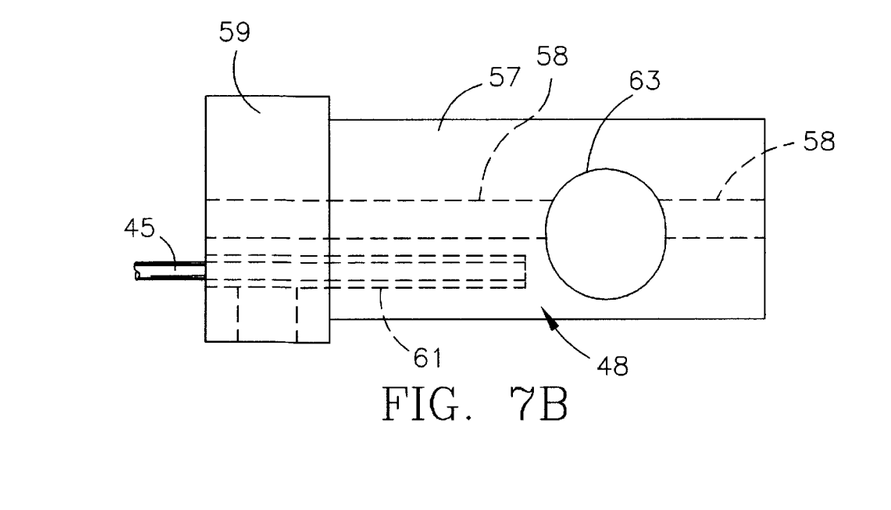
FIG. 7B is a plan view of the slide of FIG. 7A.
Figure 7C:
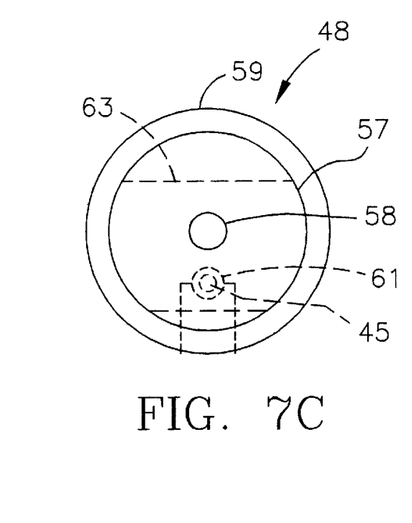
FIG. 7C is an end view of the slide of FIGS. 7A and 7B.
Figure 8A:
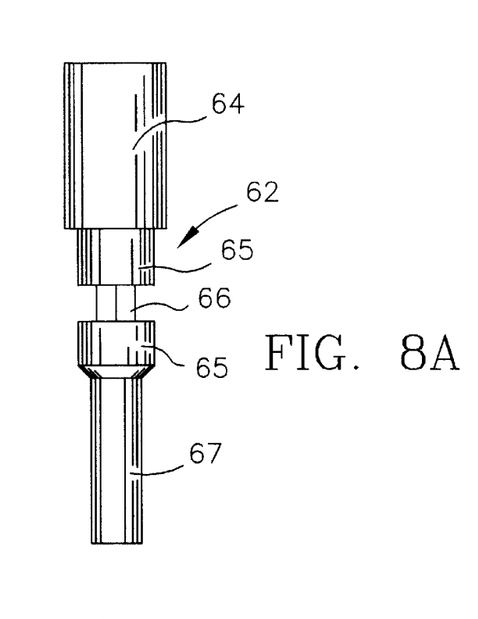
FIG. 8A is a plan view, on an enlarged scale, of a cam/axle member used in the control end (FIG. 3) of the arthroscope of FIG. 1.
Figure 8B:
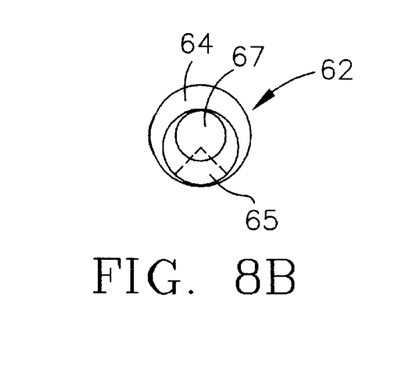
FIG. 8B is an end view of the cam/axle member of FIG. 8A.
Figure 8C:
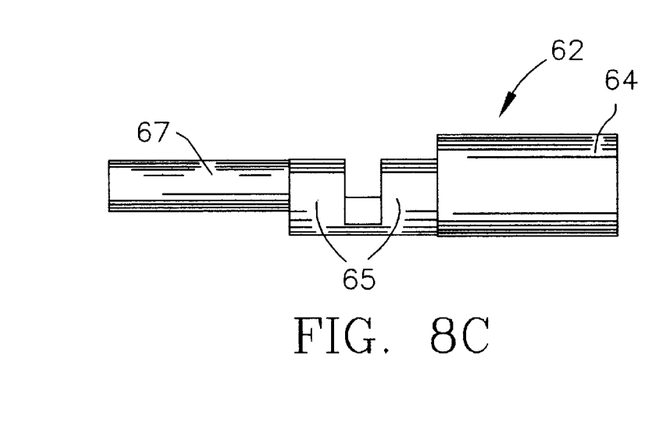
FIG. 8C is an elevation view of the cam/axle member of FIG. 8A.

The cam portion 65 of cam/axle member 62 is positioned in a central transverse opening 63 in slide 48; see FIGS. 7A–7C for opening 63, FIGS. 8A–8C for cam/axle member 62.

Opening 63 is not quite circular in cross-section; it is enlarged or "stretched" slightly, as is most apparent in FIG.

Figure 9A:
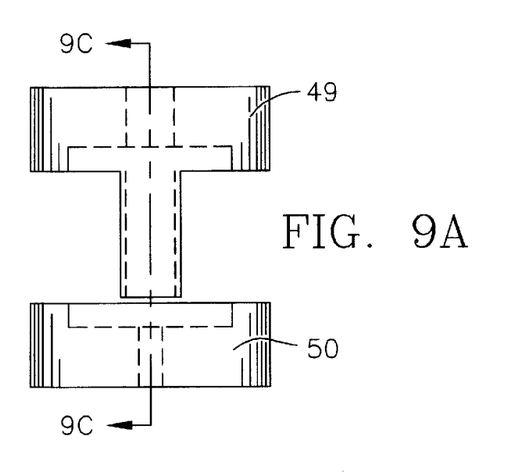
FIG. 9A is a plan view, on an enlarged scale, of two control knobs from the control end (FIG. 3) of the arthroscope of FIG. 1.
Figure 9B:
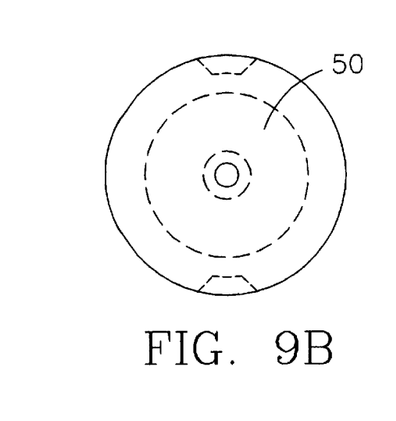
FIG. 9B is an end view of the control knobs of FIG. 9A.
Figure 9C:
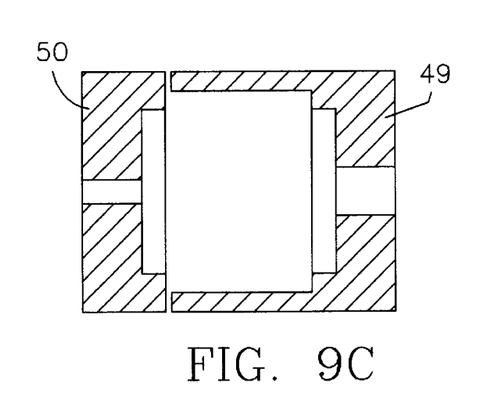
FIG. 9C is a section view, taken approximately along line 9C—9C in FIG. 9A, of the control knobs.

7B. The cam/axle member 62 includes a large control knob shaft attachment segment 64 of circular cross-section, cam segment 65 contains a relay lens assembly slot 66, and a small control knob shaft attachment segment 67. This preferred construction is shown in detail in FIGS. 8A–8C. Two control knobs, shown in FIGS. 9A–9C, are mounted on the outer ends 64 and 67 of cam/axle member 62 (FIGS. 8A–8C). The control knobs include a right-hand control knob 49 that is fitted onto the large control wheel shaft attachment segment 64 of the cam/axle member 62. The second or left-hand control knob 50 fits onto the smaller control knob shaft attachment segment 67 of cam/axle member 62. See FIGS. 8A–8C, 9A–9C and 12A–12D.

Figure 12A:
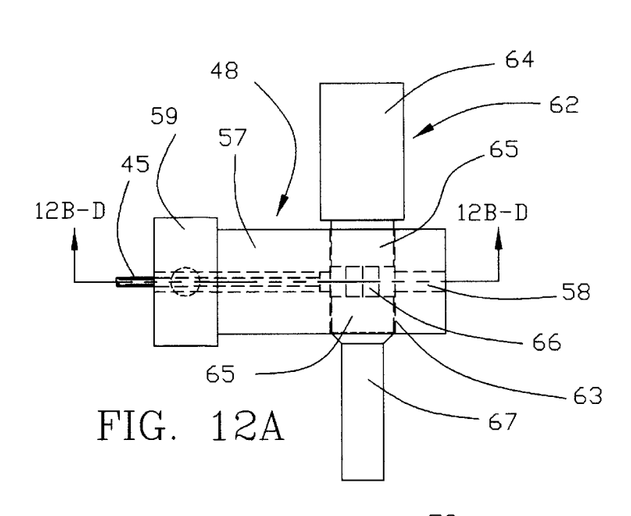
FIG. 12A is a plan view of the slide and cam/axle member used in the control end (FIG. 3) of the arthroscope of FIG. 1 shown in a center position.
Figure 12B:
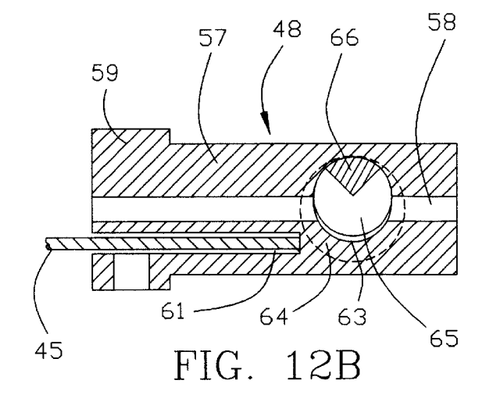
FIG. 12B is a cross-sectional view taken along line 12B–D of FIG. 12A and shown in a center position.
Figure 12C:
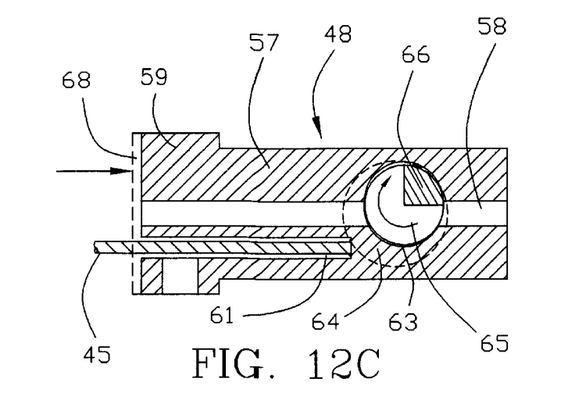
FIG. 12C is a cross-sectional view taken along line 12B–D of FIG. 12A and showing the slide in a moved position to the right of its position of FIG. 12A.
Figure 12D:
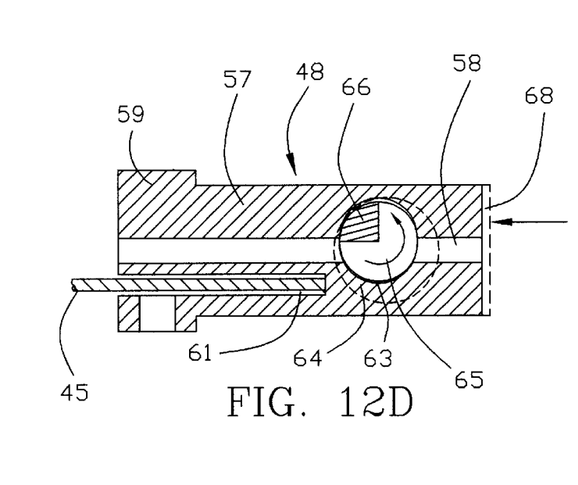
FIG. 12D is a cross-sectional view taken along line 12B–D of FIG. 12A and showing the slide in a moved position of FIG. 12A.

The control knobs 49 and 50 and their shaft attachments 64 and 67, respectively, may be connected to each other by conventional means. Either of the control knobs 49 and 50 can be used to rotate cam 65 within slide opening 63, thus causing slide 48 and the attached control rod 45, to move linearly in relation to the rotational motion of cam/axle 62 through a distance 68 as shown in FIGS. 12C and 12D. FIG. 12C shows the slide 48 moved to a rearward position closest to the control end 33 of the housing tube 31. FIG. 12D shows the slide 48 moved to a forward position closest to the image input end 32 of the housing tube 31.

Figure 10:
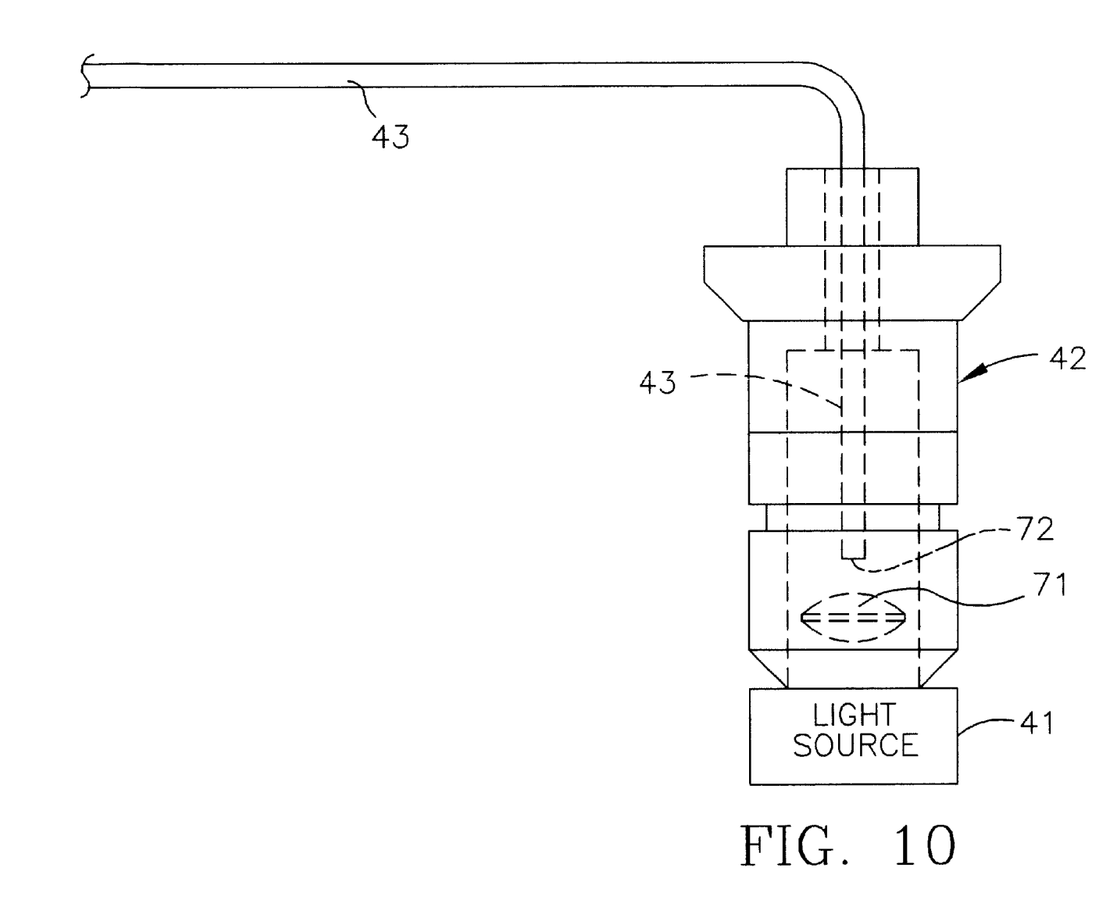
FIG. 10 is an elevation view, on an enlarged scale, of the lighting apparatus for the arthroscope of FIG. 1.

The lighting assembly 42, illustrated in FIG. 2 and shown in greater detail in FIG. 10, may include a condenser lens 71 to focus light from a suitable source 41 onto one end 72 of the light bundles 43 that extend to the input end of the arthroscope 30. See FIG. 6D. Actually, there may be two or more fiber optic light bundles 43; to supply light to the input end of arthroscope 30. As previously noted, the lighting assembly may be quite conventional in construction and hence has been described only generally.

Operation of the arthroscope 30, (FIGS. 1–10), can now be considered. At the outset, light from source 41 (FIG. 2) is focused upon the end 72 of one or more fiber optic bundles 43, as by an appropriate lens 71 (FIG. 10). As a consequence, a surgical working area just beyond the input end 32 of the arthroscope 30 (FIGS. 1 and 2) is illuminated. In arthroscope 30, illumination is effected through input lens 37 (FIGS. 6A–6C). Light from bundle(s) 43, at least in part, reflects from the fixed mirror 51, 52 onto the reflective surface 47 of the movable mirror, and through the input lens 37 into the area to be illuminated.

A light image reflected from the surgical working area, after passing through input lens 37, impinges on the inclined reflective surface 47 of the movable mirror 46, 47. That light image is directed from the movable mirror surface 47 to impinge upon the reflective surface 52 of the fixed mirror 51. From the fixed mirror the light image is re-directed toward the input end 53A of the relay lens assembly 53; see FIGS. 6A–6D. The relay lens system 53 supplies the image to the CCD attachment 36, through focusing lens assembly 55, to be viewed by the surgeon or other person using the arthroscope 30.

If the person using arthroscope 30 is dissatisfied with the image available through the CCD attachment 36, control knobs 49 and/or 50 may be used to vary the image. That is, the control knobs, through cam/axle member 62 (FIGS. 8A–8C), slide 48 (FIGS. 7A–7C), and rod 45 (FIGS. 6A–6C) can be used to advance the movable mirror 46, 47 toward the input lens 37 (see FIG. 6A), or to retract the movable mirror from the input lens (see arrow A in FIGS. 6B and 6C) to a "lower" position. In this way the image supplied to the surgeon or other person using the instrument 30 can be and is varied to a substantial extent with no change in the position of the instrument. In effect, the overall viewing range of the instrument 30 is enhanced by at least thirty degrees with no need to reposition the instrument axially. Further correction of the image can be afforded by appropriate software.

Figure 11A:
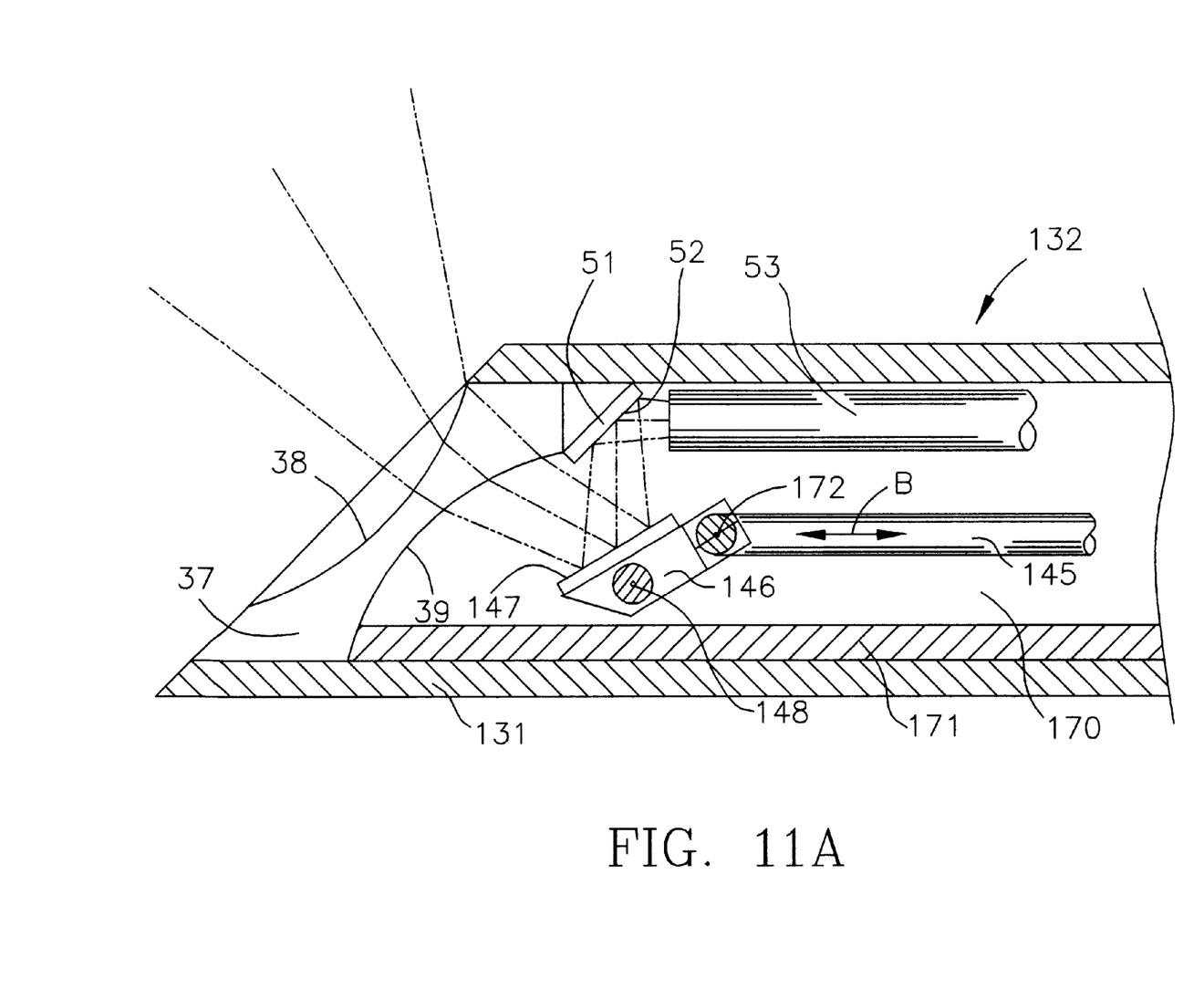
FIG. 11A is a longitudinal sectional elevation view, like FIG. 6A, of the input (viewing) end of an arthroscope comprising another embodiment of the invention, adjusted for a maximum upward view.
Figure 11B:
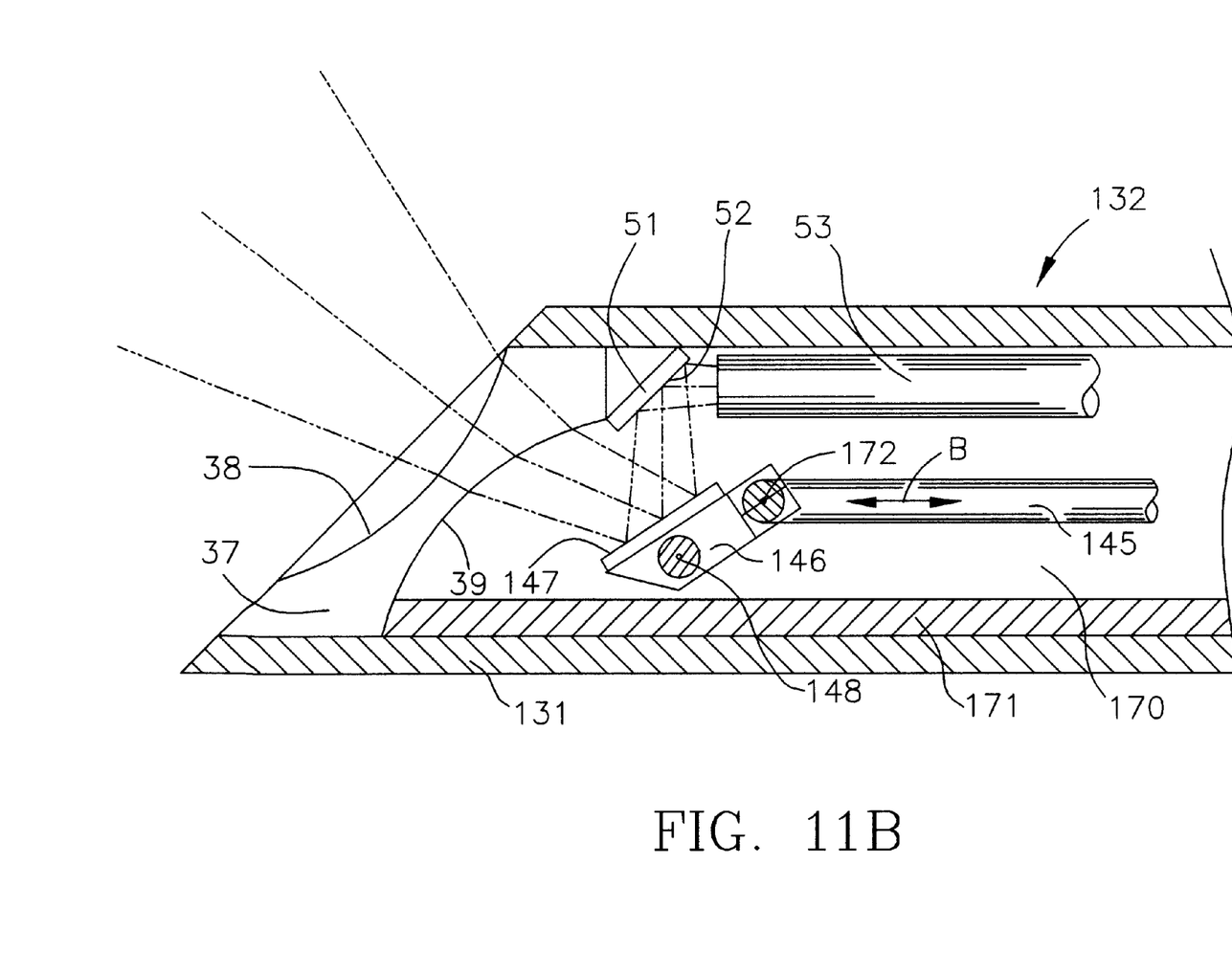
FIG. 11B is a sectional elevation view, like FIG. 11A, of the apparatus of FIG. 11A adjusted for an intermediate view.
Figure 11C:
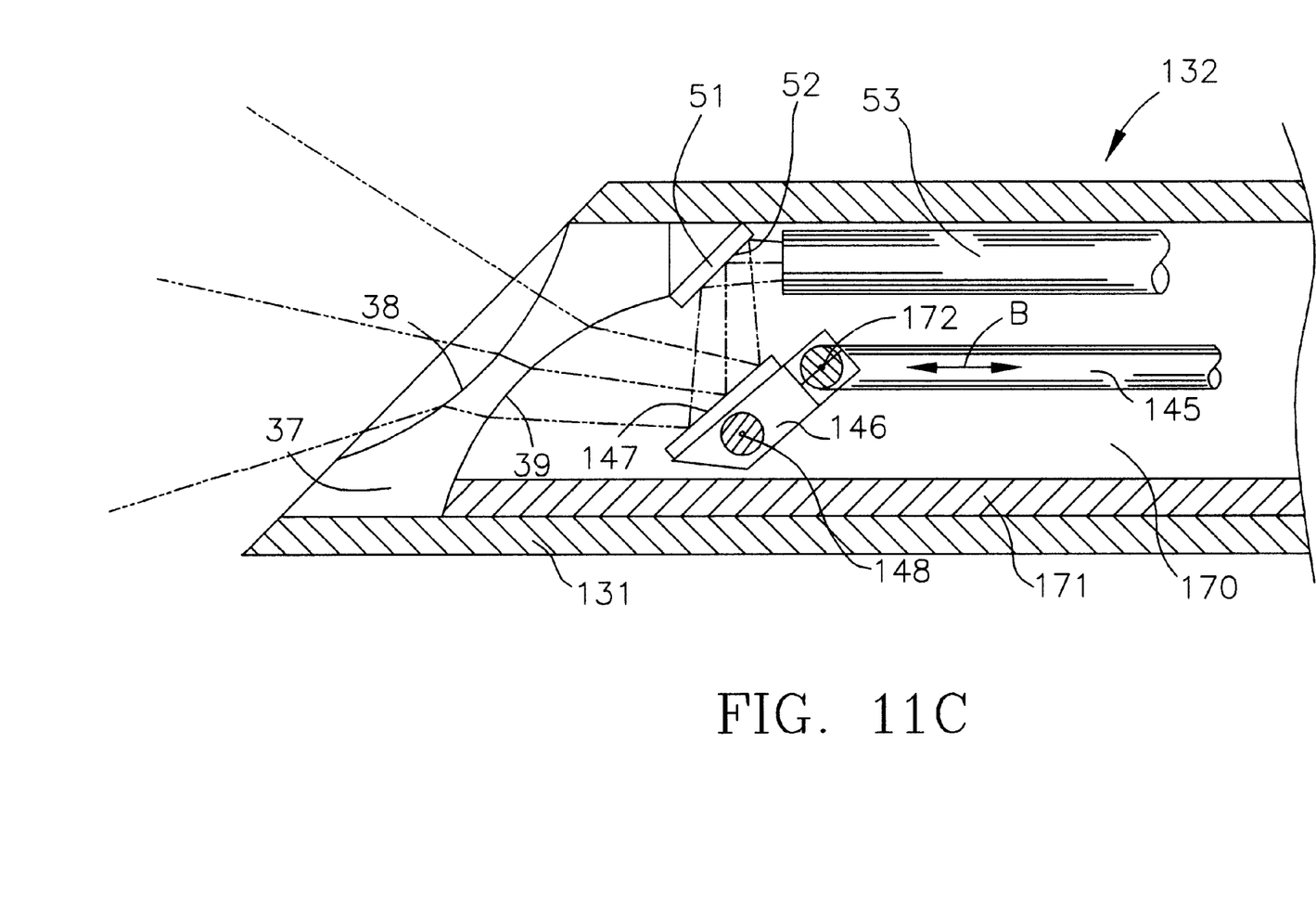
FIG. 11C is a sectional elevation view, like FIG. 11A, adjusted for a maximum downward view.

FIGS. 11A, 11B and 11C afford sectional elevation views of the input end 132 of a modified instrument; thus, FIGS. 11A, 11B and 11C correspond to FIGS. 6A, 6B and 6C, respectively. In FIGS. 11A–11C, the reference numerals and illustrated elements correspond to those employed in FIGS. 6A–6C, except for those elements that have been modified. Thus, the instrument input end 132 of a housing tube 131 is beveled, as previously described, and is closed by an input lens 37. The input lens 37 may have two concave lens surfaces, an outer surface 38 and an inner surface 39 as shown; other input lens structures may be used. A fixed mirror base 51 is mounted in the upper portion of housing tube 31, immediately adjacent input lens 37; the fixed mirror base 51 has a reflective coating on its surface 52 that faces the input end 53A of a relay lens assembly 53.

In the modification shown in FIG. 11A, there is a pivotally movable mirror comprising a base 146 having a reflective surface 147. The mirror base 146 is pivotally mounted on a shaft 148 that extends transversely of the instrument between the two sides 170 (only one shown) of a generally U-shaped support member 171 positioned in the lower part of housing tube 131. The movable mirror base 146 is connected to the end of a control rod 145, as by a pin 172; rod 145 is similar to rod 45. The control rod 145 can be moved linearly as indicated by arrow B in FIGS. 11A, B and C.

The views of FIG. 11B and FIG. 11C are the same as FIG. 11A except that FIG. 11B shows the pivotally movable mirror 146, 147 at an intermediate position, for an intermediate image, and FIG. 11C shows the pivotally movable mirror 146, 147 positioned for a maximum "downward" view. It should be understood that FIGS. 11A–11C are assumed to be vertically oriented. They could equally well be horizontally oriented, as could FIGS. 6A–6C, so that references to "upward" and "downward" could equally well be modified to "right" and "left", or vice versa. Because the control rod 145 acts as previously described for rod 45, and because only the movable mirror has been changed, from linear movement to rotational movement, it is believed to be unnecessary to provide any further description, structural or operational, of the arrangement shown in FIGS. 11A–11C.

Several parts of instrument 30 can be changed from those illustrated without appreciable effect on overall operation of instrument 30. For example, input lens 37, the shape of the movable mirrors 46, 47 and 146, 147 and the illustrated relay lens assembly 53 can be changed, as can the lighting assembly 42, 43. It will be recognized that the control rod 45 (or rod 145) may be modified; it constitutes a preferred mechanism for operating the movable mirror but any desired alternative that will move that mirror, whether linearly or along a pivotal or other required path, can be used. The angle of the level of the outer end of housing tube 31 may be varied as desired; a level of 30° to 60° is preferred, but may depend on the primary use for instrument 30. It will be recognized that use of a CCD unit for a display is not essential. The "software" used for the display may vary appreciably. Any preferred technique to enable the instrument user to move the movable mirror over its operational range is acceptable.

What is claimed is:

1. A variable view arthroscope comprising:

an elongated housing tube having an image input end spaced from an outer control end, an input lens closing said image input end of said housing tube, a lighting apparatus for illuminating a working image area beyond said image input end of said housing tube, a movable mirror intercepting light, constituting a working image, reflected from said working image area through said input lens, a control mechanism for varying the position of said movable mirror between a first limit position and a second limit position, said control mechanism including an elongated rod extending longitudinally through said housing tube between said control end and said image input end, a slide mounted in said housing tube for movement between said control end and said image input end, said elongated rod connected to said slide, a transverse passage formed in said slide with said passage having an interior wall surface, a control mechanism shaft rotatably mounted in said transverse passage, a cam surface mounted on said control mechanism shaft with said cam surface engaged with said interior wall surface of said transverse passage of said slide so that rotation of said control mechanism shaft will selectively move said slide in a direction toward control end or in a direction toward said image input end of said elongated housing tube, a fixed mirror positioned to intercept light from said movable mirror, redirecting said light towards a relay lens location within said housing tube near said input end thereof, and a relay lens assembly, having an input end near said fixed mirror position, for directing light from said fixed mirror through said housing tube towards a focusing receptor located adjacent said control end of said housing tube.

2. A variable view arthroscope, according to claim 1, in which said input lens is a diverging lens.

3. A variable view arthroscope, according to claim 1 in which said input lens is an image-expanding lens.

4. A variable view arthroscope, according to claim 1, in which said image input end of said housing tube is beveled at an angle of about 30° to about 60°; and said input lens extends across said beveled input end of said housing tube.

5. A variable view arthroscope, according to claim 1, in which said lighting apparatus radiates light through said input lens toward said working image area.

6. A variable view arthroscope, according to claim 1, in which said movable mirror moves by sliding towards and away from said input lens to modify said working image.

7. A variable view arthroscope, according to claim 6, in which said movable mirror has at least three positions, and further comprising:

a mechanism at said control end of the housing establishing two of said positions at said first and second limit positions for said movable mirror and at least one intermediate position between said first and second positions.

8. A variable view arthroscope, according to claim 1, in which said movable mirror is a concave mirror.

9. A variable view arthroscope, according to claim 1, in which said movable mirror moves by rotating about an axis transverse to the input end of the housing tube.

10. A variable view arthroscope, according to claim 9, in which said movable mirror has at least three positions, and further comprising:

a mechanism at said control end of said housing for establishing two of said positions at said first and second limit positions for said movable mirror and at least one intermediate position between said first and second positions.

11. A variable view arthroscope, according to claim 1, in which said relay lens is located in said image end of said housing tube with an input surface adjacent to said fixed mirror.

12. A variable view arthroscope, according to claim 11, in which:

said relay lens assembly comprises an elongated optical guide, having an input end and an output end, said relay lens assembly extending from said input image end of said housing tube to said control end thereof; and a focusing lens located adjacent said control end of said housing tube for focusing an image from said output end of the optical guide onto a CCD device.

13. A variable view arthroscope, according to claim 12, in which said focusing lens works with an image-erecting prism.

* * * * *